US011308609B2

(12) United States Patent
Annangi et al.

(10) Patent No.: US 11,308,609 B2
(45) Date of Patent: Apr. 19, 2022

(54) SYSTEM AND METHODS FOR SEQUENTIAL SCAN PARAMETER SELECTION

(71) Applicant: GE Precision Healthcare LLC, Milwaukee, WI (US)

(72) Inventors: Pavan Annangi, Bangalore (IN); Hariharan Ravishankar, Bangalore (IN); Tore Bjaastad, Molde (NO); Erik Normann Steen, Moss (NO); Svein Arne Aase, Trondheim (NO); Rohan Patil, Bangalore (IN)

(73) Assignee: GE Precision Healthcare LLC, Milwaukee, WI (US)

(*) Notice: Subject to any disclaimer, the term of this patent is extended or adjusted under 35 U.S.C. 154(b) by 109 days.

(21) Appl. No.: 16/703,547

(22) Filed: Dec. 4, 2019

(65) Prior Publication Data

US 2021/0174496 A1    Jun. 10, 2021

(51) Int. Cl.
    *G06T 7/00*      (2017.01)
    *A61B 8/08*      (2006.01)

(52) U.S. Cl.
    CPC ......... *G06T 7/0012* (2013.01); *A61B 8/5207* (2013.01); *A61B 8/5223* (2013.01);
    (Continued)

(58) Field of Classification Search
None
See application file for complete search history.

(56) References Cited

U.S. PATENT DOCUMENTS 6,102,859 A    8/2000   Mo
6,142,943 A   11/2000   Mo et al.
(Continued)

FOREIGN PATENT DOCUMENTS

EP    1008863 A2    6/2000
EP    1097674 A2    5/2001

OTHER PUBLICATIONS

J. A. Hossack, "Extended focal depth imaging for medical ultrasound," 1996 IEEE Ultrasonics Symposium. Proceedings, 1996, pp. 1535-1540 vol.2, doi: 10.1109/ULTSYM.1996.584375. (Year: 1996).*
(Continued)

*Primary Examiner* — Vu Le
*Assistant Examiner* — Courtney Joan Nelson
(74) *Attorney, Agent, or Firm* — McCoy Russell LLP

(57) ABSTRACT

Methods and systems are provided for sequentially selecting scan parameter values for ultrasound imaging. In one example, a method includes selecting a first parameter value for the a first scan parameter based on an image quality of each ultrasound image of a first plurality of ultrasound images of an anatomical region, each ultrasound image of the first plurality of ultrasound images having a different parameter value for the first scan parameter, selecting a second parameter value for a second scan parameter based on an image quality of each ultrasound image of a second plurality of ultrasound images of the anatomical region, each ultrasound image of the second plurality of ultrasound images having a different parameter value for the second scan parameter, and applying the first parameter value for the first scan parameter and the second parameter value for the second scan parameter to one or more additional ultrasound images.

11 Claims, 8 Drawing Sheets

(52) U.S. Cl.
CPC ............ *G06T 2207/10028* (2013.01); *G06T 2207/10132* (2013.01); *G06T 2207/20084* (2013.01)

(56) References Cited

U.S. PATENT DOCUMENTS

| | | | |
|---|---|---|---|
| 7,062,714 | B1 | 6/2006 | Mo et al. |
| 8,235,905 | B2 * | 8/2012 | Lin ................ G01S 7/5205 600/443 |
| 8,357,094 | B2 | 1/2013 | Mo et al. |
| 8,784,318 | B1 | 7/2014 | Napolitano et al. |
| 9,901,323 | B2 | 2/2018 | Napolitano et al. |
| 10,074,038 | B2 * | 9/2018 | Hsieh ................ G06T 7/0002 |
| 2008/0123992 | A1 * | 5/2008 | Tian ................ G06T 15/08 382/276 |
| 2014/0221832 | A1 | 8/2014 | El-Zehiry et al. |
| 2015/0254866 | A1 * | 9/2015 | Mendonca ........ G06K 9/3233 382/132 |
| 2017/0086785 | A1 * | 3/2017 | Bjaerum ................ A61B 8/13 |

OTHER PUBLICATIONS

Yap, M. et al., "Object Boundary Detection in Ultrasound Images," Proceedings of the 3rd Canadian Conference on Computer and Robot Vision (CRV'06), Jun. 7, 2006, Quebec, Canada, 6 pages.

Rangaraju, K. et al., "Review Paper on Quantitative Image Quality Assessment—Medical Ultrasound Images," International Journal of Engineering Research & Technology (IJERT), vol. 1, No. 4, Jun. 2012, 6 pages.

Rahmatullah, B. et al., "Integration of Local and Global Features for Anatomical Object Detection in Ultrasound," Proceedings of the 15th International Conference on Medical Image Computing and Computer-Assisted Intervention (MICCAI 2012), Oct. 1, 2012, Nice, France, 8 pages.

El-Zehiry, N. et al., "Learning the Manifold of Quality Ultrasound Acquisition," Proceedings of the 16th International Conference on Medical Imaging Computing and Computer-Assisted (MICCAI 2013), Sep. 22, 2013, Nagoya, Japan, 8 pages.

Zhang, L. et al., "Automatic image quality assessment and measurement of fetal head in two-dimensional ultrasound image," Journal of Medical Imaging, vol. 4, No. 2, Apr. 17, 2017, 11 pages.

* cited by examiner

SYSTEM AND METHODS FOR SEQUENTIAL SCAN PARAMETER SELECTION

TECHNICAL FIELD

Embodiments of the subject matter disclosed herein relate to ultrasound imaging, and more particularly, to improving image quality for ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method includes selecting a first parameter value for the a first scan parameter based on an image quality of each ultrasound image of a first plurality of ultrasound images of an anatomical region, each ultrasound image of the first plurality of ultrasound images having a different parameter value for the first scan parameter, selecting a second parameter value for a second scan parameter based on an image quality of each ultrasound image of a second plurality of ultrasound images of the anatomical region, each ultrasound image of the second plurality of ultrasound images having a different parameter value for the second scan parameter, and applying the first parameter value for the first scan parameter and the second parameter value for the second scan parameter to one or more additional ultrasound images.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
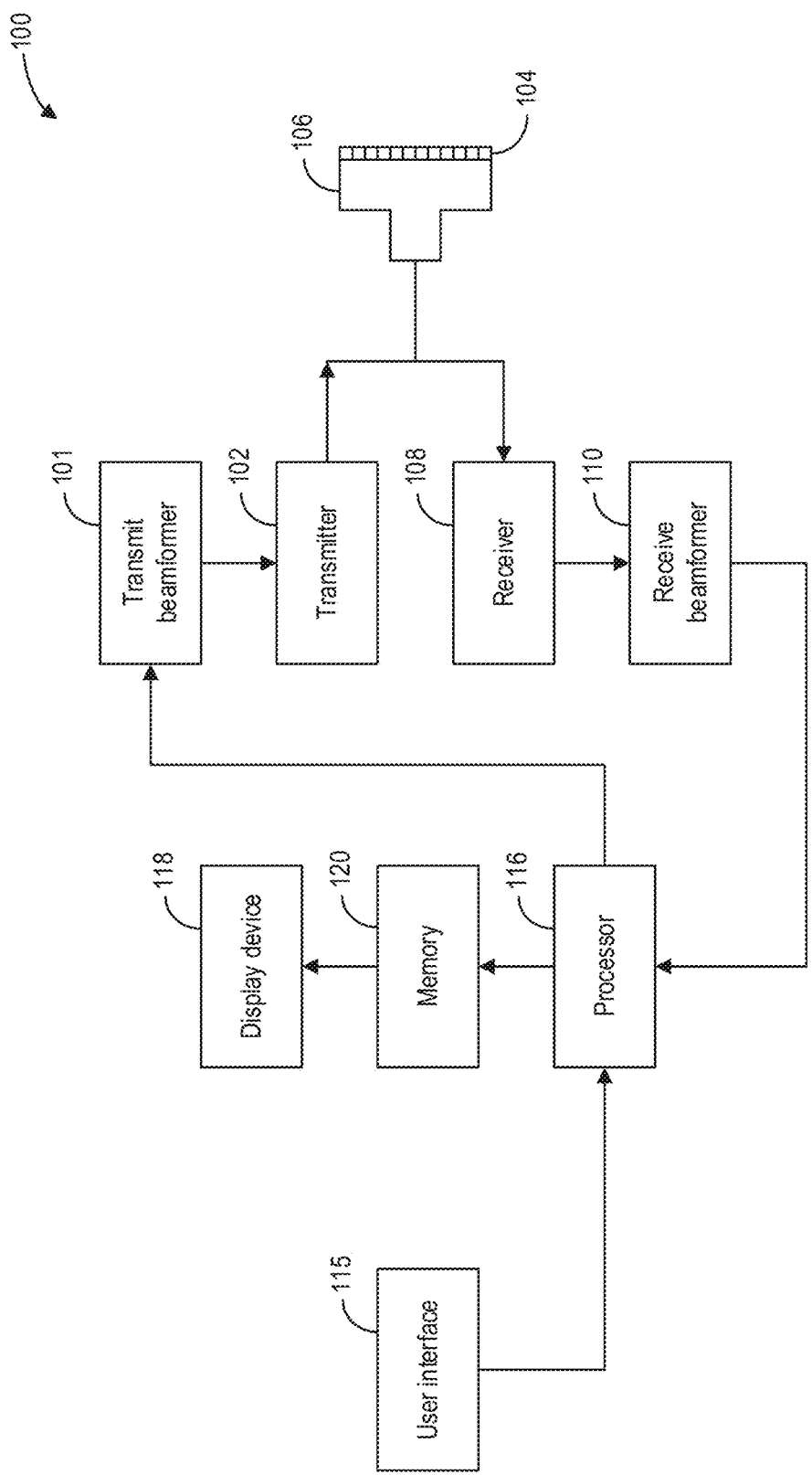
FIG. 1 shows a block diagram of an exemplary embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of the target anatomical feature (e.g., the heart, the liver, the kidney, or another anatomical feature). The acquisition parameters that may be adjusted include transmit frequency, transmit depth, gain, beam steering angle, beamforming strategy, and/or other parameters. Varying the acquisition parameters to acquire an optimal image (e.g., of desired quality) can be very challenging and is based on user experience. Image quality variations with acquisition parameters is not a well-studied problem. Thus, the adjustment of the acquisition parameters by the operator in order to acquire an optimal image is often subjective. For example, the operator may adjust various acquisition parameters until an image is acquired that looks optimal to the operator, and the process of adjusting the acquisition parameters may not be defined or repeated from exam to exam. Further, various post-acquisition image parameters that may affect image quality are also adjustable by the operator, such as bandwidth and center frequency of the filtering of the received ultrasound data. This subjectivity and lack of a defined process may lead to irreproducible results and, in many ultrasound exams, images that are as high quality as possible may not be acquired.

Thus, according to embodiments disclosed herein, the problem of image acquisition parameter optimization and/or image post-acquisition processing optimization is addressed via a feedback system based on an automated image quality measurement algorithm that is configured to automatically identify the acquisition parameters that will generate the best possible image for the anatomy being imaged. The automated image quality measurement algorithm may include an artificial intelligence-assisted feedback system to optimize the acquisition parameters in a sequential fashion, with one parameter after the other adjusted to arrive at an optimal acquisition parameter setting based on automatically identified image quality metrics. For example, the optimal transmit depth may be selected from images acquired at several depth acquisitions based on which image has the highest, depth-specific image quality. This is followed by optimizing for frequency from images acquired at various frequency settings at the selected optimal depth based on which image as the highest, frequency-specific image quality. In doing so, the optimal acquisition parameters (e.g., depth and frequency) for a given scan plane/anatomical feature may be identified in a reproducible manner, which may increase consistency of image quality across different ultrasound exams Additionally, in some examples, different parameter values for one or more post-acquisition processing parameters may be applied to an image to generate, for each post-acquisition processing parameter, a set of replicate images that each have a different parameter value for that post-acquisition processing parameter. The image quality may be determined for each replicate image, and the replicate image having the highest image quality may be selected. The parameter value for that post-acquisition processing parameter may be set as the parameter value from the selected replicate image and applied to subsequent images. The selection of the optimal acquisition and/or post-acquisition parameters may simplify the operator's workflow, which may reduce exam time and may facilitate higher quality exams, even for more novice operators.

Figure 2:
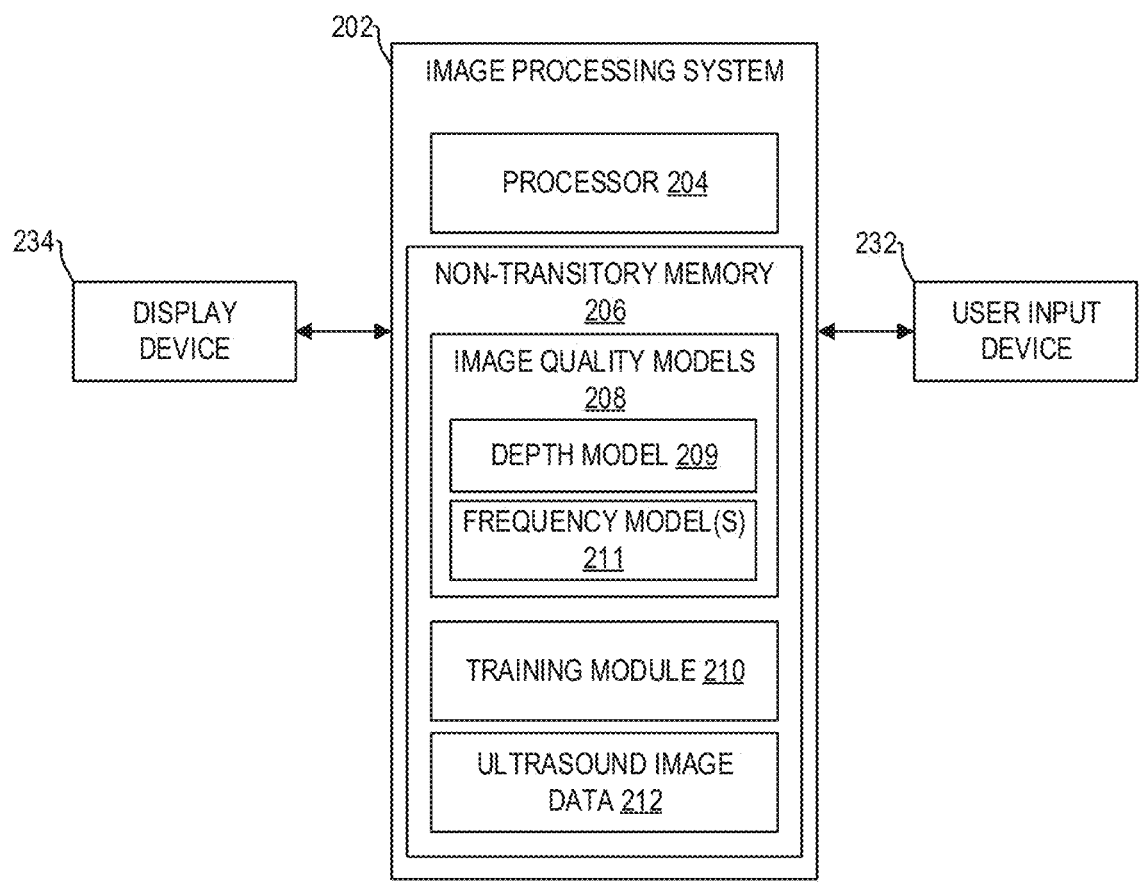
FIG. 2 is a schematic diagram illustrating a system for generating ultrasound images at optimized parameter settings, according to an exemplary embodiment.
Figure 4:
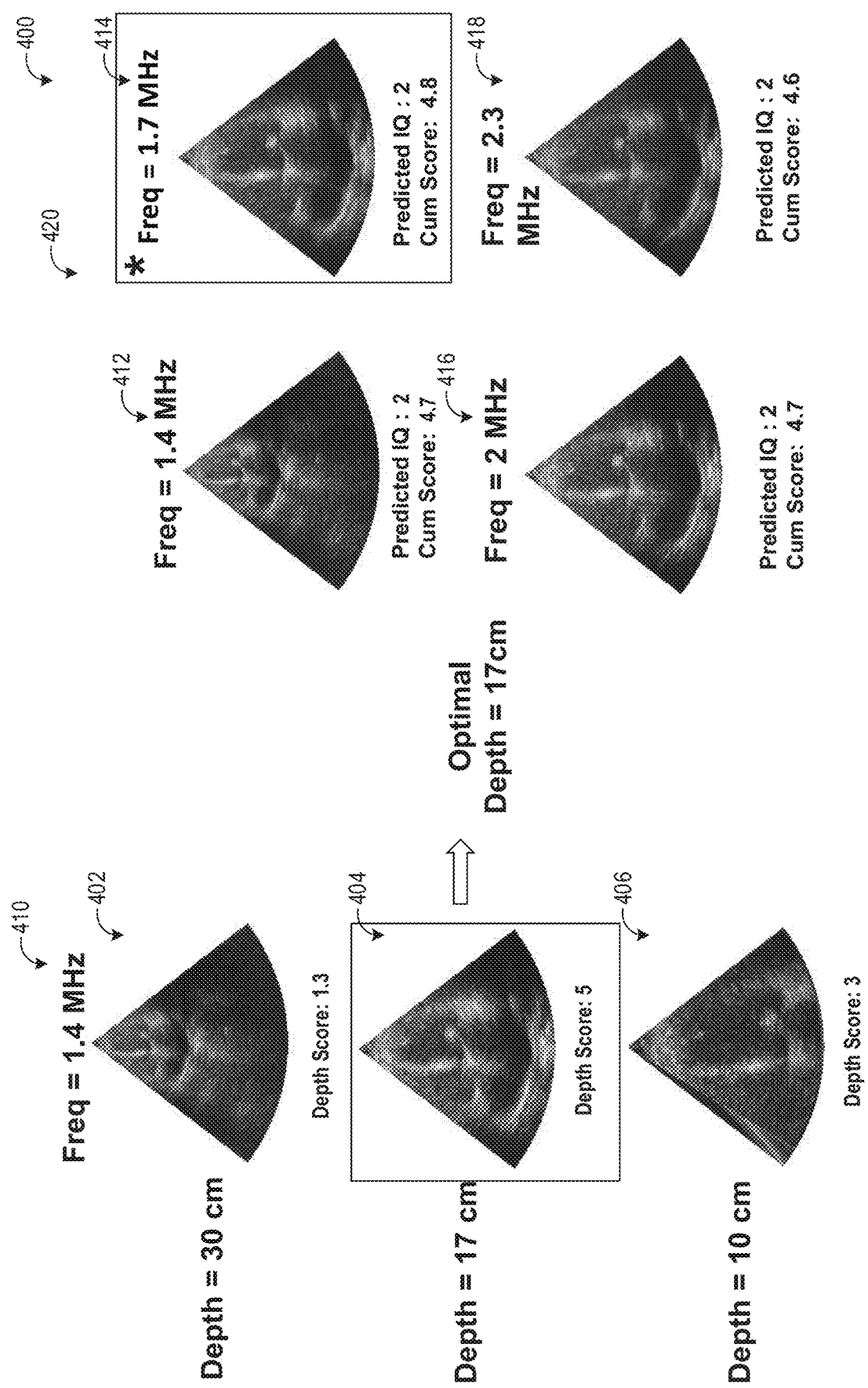
FIG. 4 shows example ultrasound images and associated image quality metrics that may be acquired according to the process of FIG. 3.
Figure 5A:
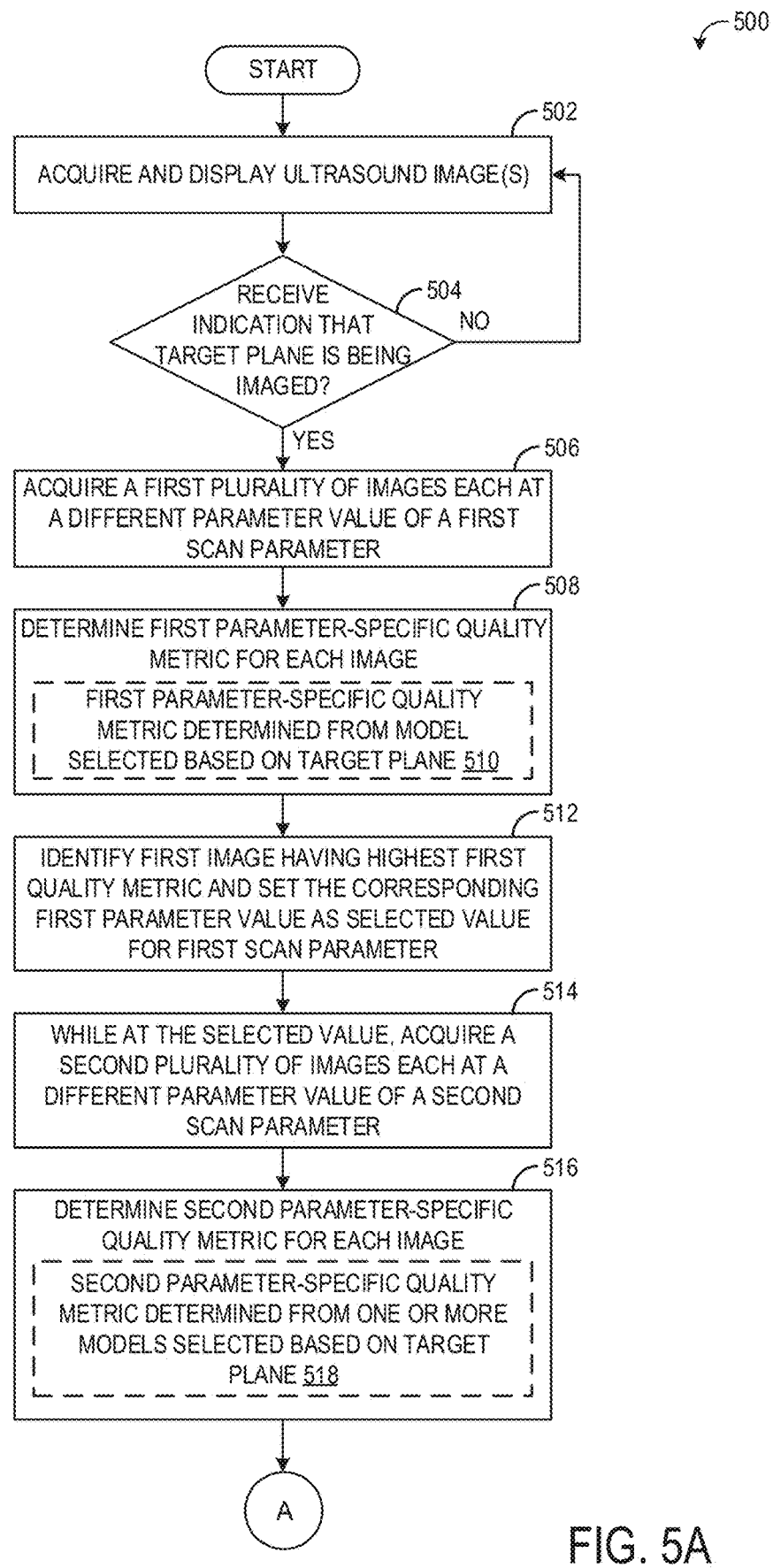
FIGS. 5A and 5B are a flow chart illustrating an example method for selecting ultrasound scan parameters during ultrasound imaging, according to an exemplary embodiment.
Figure 5B:
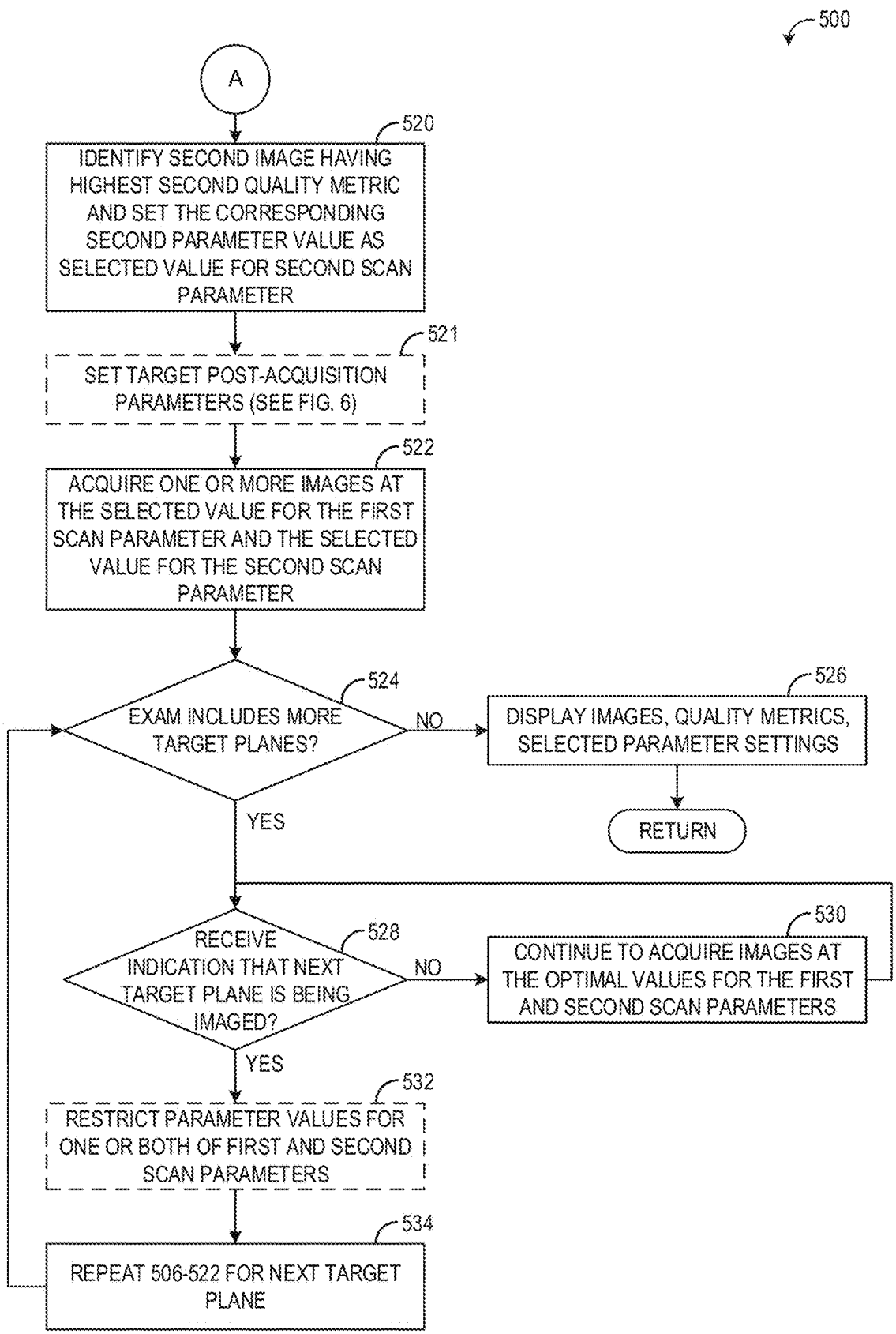
Figure 6:
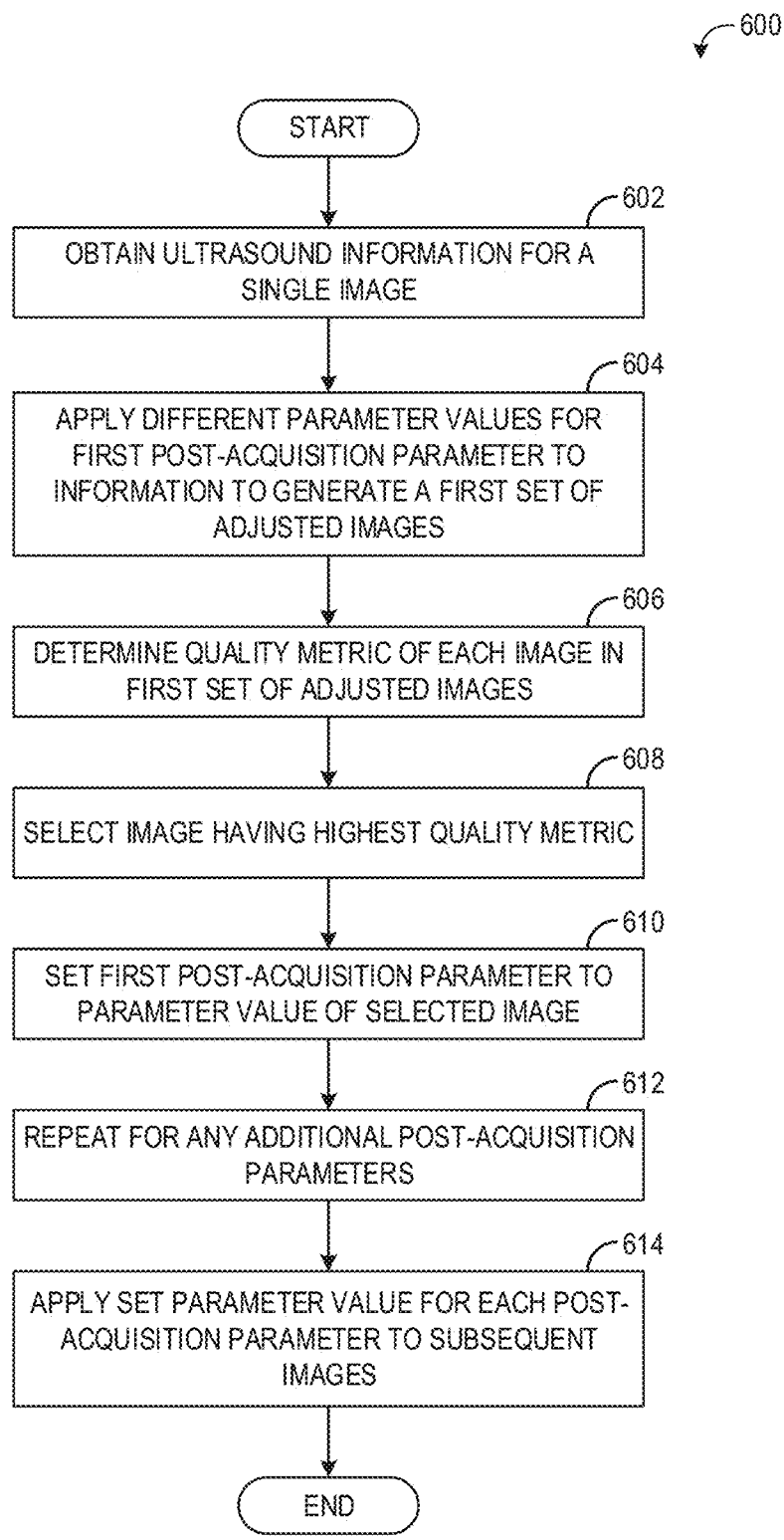
FIG. 6 is a flow chart illustrating an example method for selecting image post-acquisition processing parameters during ultrasound image.
Figure 7:
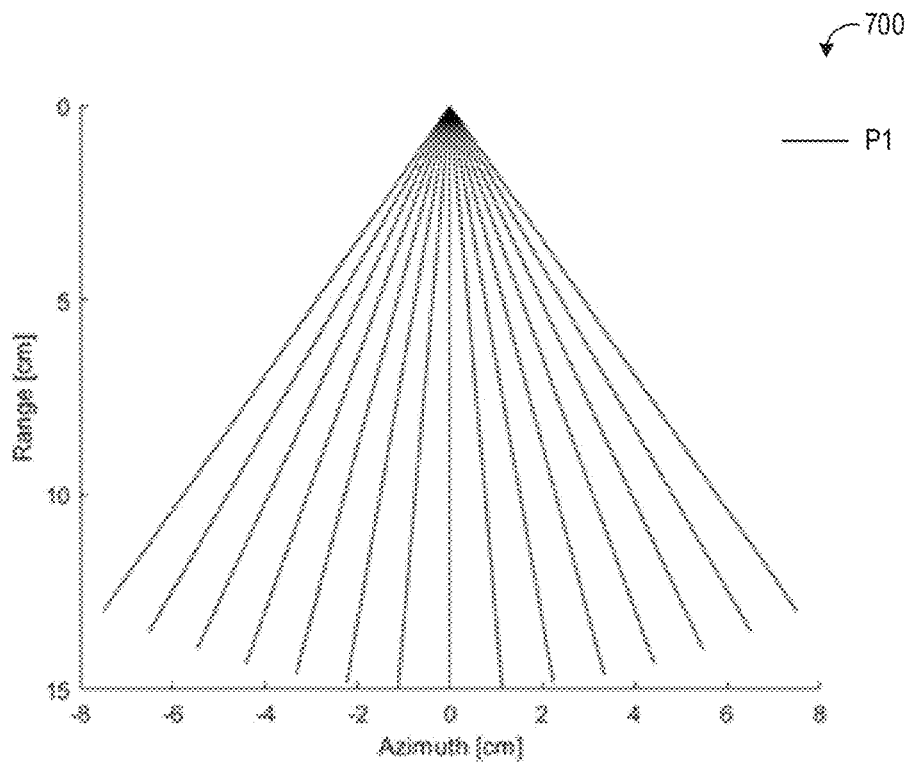
FIG. 7 is a graph showing a scan sequence for acquiring a single ultrasound image, according to an exemplary embodiment.
Figure 8:
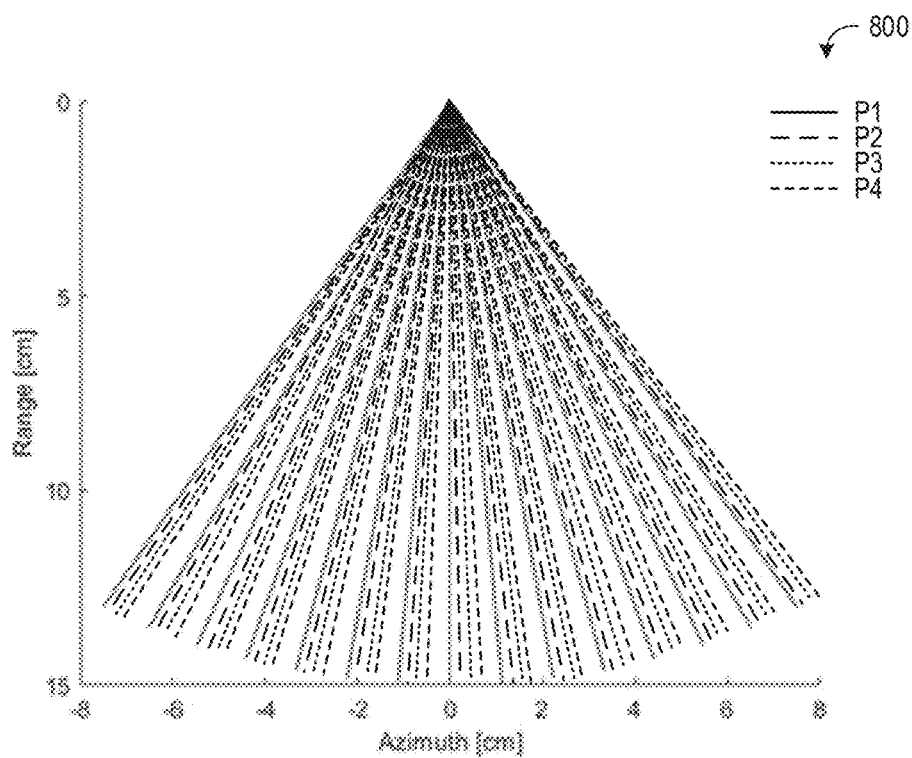
FIG. 8 is a graph showing a scan sequence for acquiring multiple ultrasound images, according to an exemplary embodiment.

An example ultrasound system including an ultrasound probe, a display device, and an imaging processing system are shown in FIG. 1. Via the ultrasound probe, ultrasound images may be acquired and displayed on the display device. As described above, the images may be acquired using various acquisition scan parameters, such as frequency and depth, which have parameter values that may be selected to increase image quality of the acquired images. To select the scan parameter values, a plurality of images acquired at different scan parameter values may be analyzed to determine which scan parameter values result in images having a highest image quality. An image processing system, as shown in FIG. 2, includes one or more image quality models, such as a depth model and one or more frequency models, which may be deployed according to the sequential process shown in FIG. 3 to determine the image quality of each of the plurality of images, as shown in FIG. 4, and select scan parameter values that will result in relatively high image quality. A method for sequentially selecting scan parameter values during ultrasound imaging is shown in FIGS. 5A and 5B. After the target scan parameter values have been selected, different post-acquisition processing parameter values may be applied to an image to create a set of adjusted images, and the image quality models may be deployed to determine which image from the set of adjusted images has the highest image quality and thus which post-acquisition processing parameter value(s) should be applied to that and/or subsequent images, as shown by the method of FIG. 6. The images disclosed herein may be acquired according to a scan sequence as shown in FIG. 7 and/or according to a scan sequence as shown in FIG. 8.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be analyzed by one or more machine learning models trained using ultrasound images and corresponding ground truth output in order to assign scan parameter-specific image quality metrics to the ultrasound images. As used herein, ground truth output refers to an expected or "correct" output based on a given input into a machine learning model. For example, if a machine learning model is being trained to classify images of cats, the ground truth output for the model, when fed an image of a cat, is the label "cat". As explained in more detail below, if a machine learning model is being trained to classify ultrasound images on the basis of an image quality factor associated with depth (e.g., visibility of certain anatomical features), the ground truth output for the model may be a label indicating a level of the image quality factor, e.g., on a scale of 1-5 with 1 being a lowest image quality level (e.g., reflecting insufficient or inadequate depth, the least optimal depth) and 5 being a highest image quality level (e.g., reflecting sufficient depth, the most optimal depth). Similarly, if a machine learning model is being trained to classify ultrasound images on the basis of an image quality factor associated with frequency (e.g., speckling), the ground truth output for the model may be a label indicating a level of the image quality factor, e.g., on a scale of 1-5 with 1 being a lowest image quality level (e.g., reflecting high/not smooth speckling, the least optimal frequency) and 5 being a highest image quality level (e.g., reflecting low/smooth speckling, the most optimal frequency).

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store image quality models 208, training module 210, and ultrasound image data 212. Image quality models 208 may include one or more machine learning models, such as deep learning networks, comprising a plurality of weights and biases, activation functions, loss functions, gradient descent algorithms, and instructions for implementing the one or more deep neural networks to process input ultrasound images. For example, image quality models 208 may store instructions for implementing a depth model 209 and/or one or more frequency models 211. The depth model 209 and one or more frequency models 211 may each include one or more neural networks. Image quality models 208 may include trained and/or untrained neural networks and may further include training routines, or parameters (e.g., weights and biases), associated with one or more neural network models stored therein.

Depth model 209 may be a neural network (e.g., a convolutional neural network) trained to identify far-field structures in the ultrasound images and determine if far-field structures (e.g., structures beyond/below the focal point of the ultrasound beam with respect to the transducers of the ultrasound probe) are at an expected depth. Depth model 209 may be trained to identify the far-field structures in a scan plane/view specific manner. For example, a depth model may be trained to identify far-field structures in a four-chamber view of a heart but not in a parasternal long axis (PLAX) view of the heart. Thus, in some examples, depth model 209 may actually comprise a plurality of depth models, each specific to a different scan plane or anatomical view. Depth model 209 may be trained to output a first image quality metric that reflects a quality of an input ultrasound image as a function of transmit acquisition depth. For example, the far-field structures identified by the depth model may change in appearance/visibility as depth is changed, and the first image quality metric output by the depth model may reflect the appearance/visibility of these structures as an indicator of whether the depth used to acquire the ultrasound image is an optimal depth.

The one or more frequency models 211 may include one or more neural networks or other machine learning models trained to output a respective second image quality metric that represents an image quality factor that changes as a function of transmit frequency. The one or more frequency models 211 may include a first frequency model that assesses speckle size (referred to as a speckle model), a second frequency model that assess key landmarks (referred to as a landmark detection model), and a third frequency model that assess global image quality relative to a population-wide library of ultrasound images (referred to as a global image quality model). The speckle model may be trained to output a speckle image quality metric that reflects a level of smoothness of speckling in the input ultrasound image. As speckling smoothness increases as frequency increases, the speckle image quality metric may increase as frequency increases. The landmark detection model may be trained to output a landmark image quality metric that reflects the appearance/visibility of certain anatomical features (landmarks) in the input ultrasound image. For example, as transmit frequency increases, certain anatomical features, such as the mitral valves, may start to decrease in image quality/appearance. Thus, the landmark detection model may identify the key landmarks in the input ultrasound image and output the landmark image quality metric based on the image quality/visibility of the identified key landmarks. Because the key landmarks change as the scan plane/anatomical view change, the landmark detection model may include a plurality of different landmark detection models, each specific to a different scan plane or anatomical view.

The global image quality model may be trained to assess the overall image quality of an input ultrasound image relative to a population-wide library of ultrasound images. For example, the global image quality model may be trained with a plurality of ultrasound images of a plurality of different patients, with each training ultrasound image annotated or labeled by an expert (e.g., cardiologist or other clinician) with an overall image quality score (e.g., on a scale of 1-5 with 1 being a lowest image quality and 5 being a highest image quality). The global image quality model, after training/validation, may then generate an output of a global image quality metric that reflects the overall image quality of an input ultrasound image relative to the training ultrasound images. By including an image quality metric that reflects image quality relative to a wider population, patient-specific image quality issues may be accounted for.

Non-transitory memory 206 may further include training module 210, which comprises instructions for training one or more of the machine learning models stored in image quality models 208. In some embodiments, the training module 210 is not disposed at the image processing system 202. The image quality models 208 thus includes trained and validated network(s).

Non-transitory memory 206 may further store ultrasound image data 212, such as ultrasound images captured by the ultrasound imaging system 100 of FIG. 1. The ultrasound image data 212 may comprise ultrasound image data as acquired by the ultrasound imaging system 100, for example. The ultrasound images of the ultrasound image data 212 may comprise ultrasound images that have been acquired by the ultrasound imaging system 100 at different parameter values for different scan parameters, such as different frequencies and/or different depths. Further, ultrasound image data 212 may store ultrasound images, ground truth output, iterations of machine learning model output, and other types of ultrasound image data that may be used to train the image quality models 208, when training module 210 is stored in non-transitory memory 206. In some embodiments, ultrasound image data 212 may store ultrasound images and ground truth output in an ordered format, such that each ultrasound image is associated with one or more corresponding ground truth outputs. However, in examples where training module 210 is not disposed at the image processing system 202, the images/ground truth output usable for training the image quality models 210 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
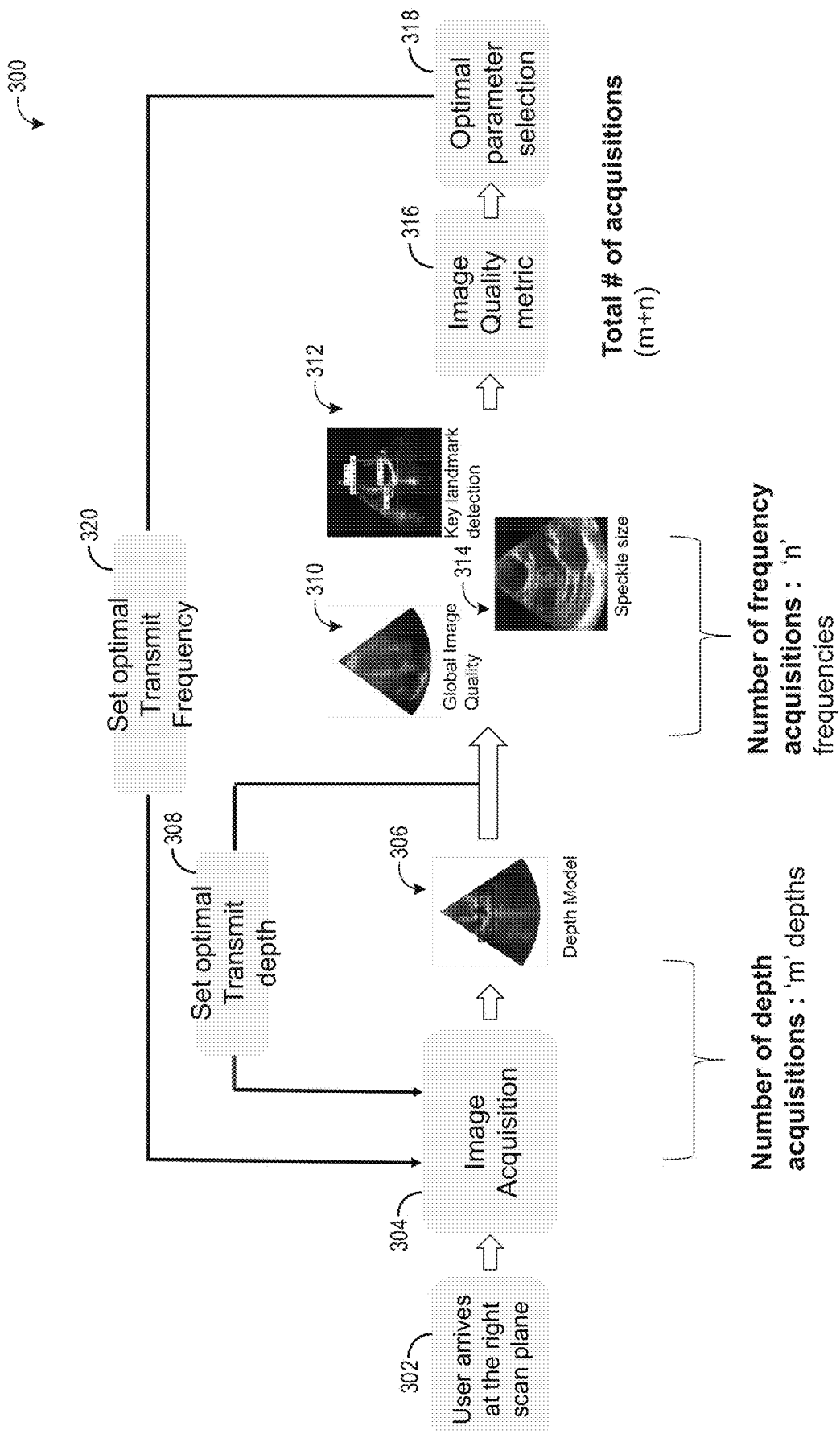
FIG. 3 is a schematic diagram illustrating a process for selecting ultrasound scan parameters, according to an exemplary embodiment.

Turning to FIG. 3, it shows a process 300 for sequentially selecting scan parameter values for two scan parameters, herein depth and frequency. The scan parameter values may be selected according to which scan parameter values result in a highest image quality, where the image quality is determined by machine learning models. Process 300 may be carried out with the components of FIGS. 1-2 (e.g., images may be acquired via ultrasound probe 106 and the parameter value selection may be carried out by image processing system 202). As shown, image acquisition may commence at 304 once the operator of the ultrasound system positions the ultrasound probe to image a target scan plane (shown at 302). The image acquisition may include acquiring a first plurality of images, with each image of the first plurality of images acquired at a single frequency (e.g., 1.4 Mz) and a different depth value (e.g., a first image at 30 cm, a second image at 17 cm, and a third image at 10 cm). Each image of the first plurality of images is entered into a depth model 306, which may be a non-limiting example of depth model 209 of FIG. 2. The depth model 306 may be a machine learning model, such as a neural network, trained to determine a first image quality score that reflects a quality of an input image from the perspective of whether one or more key anatomical features in the target scan plane are sufficiently visible/of high enough quality. The one or more key anatomical features may be features that change in visibility/quality as depth changes, and thus may be used as a marker for which depth value may result in a high quality image. The image from the first plurality of images having the highest first image quality score may be selected, and the depth at which that image was acquired may be chosen as a selected depth value to be used for subsequent image acquisition. If there are two or more images having the same, highest first image quality score, the image acquired at the largest depth may be selected.

Once a selected depth value is identified, the transmit depth of the ultrasound probe may be adjusted to the selected (e.g., optimal) depth value at 308, and a second plurality of images is acquired. Each image of the second plurality of images is acquired at the selected depth value, and at a different frequency value (e.g., a first image may be acquired at 1.4 MHz, a second image may be acquired at 1.7 MHz, a third image may be acquired at 2 MHz, and a fourth image may be acquired at 2.3 MHz). Each image of the second plurality of images is entered into one or more models to determine a second image quality score for each image of the second plurality of images. The one or more models may include a global image quality model 310, a landmark detection model 312, and a speckle model 314 (which may be non-limiting examples of the global image quality model, landmark detection model, and speckle model described above with respect to FIG. 2). Each of the global image quality model 310, landmark detection model 312, and speckle model 314 may be a machine learning model, such as a neural network. The global image quality model 310 may be trained to assign a score (e.g., on a scale of 1-5) to each image based on the image quality of that image in a population-wide manner. The landmark detection model 312 and speckle model 314 may each output scores that reflect how much a given patient's images change in quality as a function of ultrasound transmit frequency, as speckles on ultrasound images may smooth/change in size as frequency increases and certain key anatomical landmarks may become more or less visible as frequency changes. The scores output from each model may be combined to generate a cumulative, second image quality score as shown at 316. The image from the second plurality of images having the highest second image quality score may be selected at 318, and the frequency at which that image was acquired may be chosen as a selected frequency value for subsequent image acquisition. If there are two or more images having the same, highest second image quality score, the image acquired at the highest frequency may be selected.

Any additional images of that target scan plane or view desired by the operator and/or dictated by a scanning protocol may be acquired at the selected depth value and the selected (e.g., optimal) frequency value, as shown at 320.

The sequential process shown in FIG. 3 may result in a total of m+n images being acquired in order to select the depth value and frequency value for subsequent acquisition. The m number of images may be based on how many depth values are available/selected to be optimized. As described above, there may be three possible depth values, but other numbers of depth values may be possible, such as two or four or more. Likewise, the n number of images may be based on how many frequency values are available/selected to be optimized. As described above, there may be four possible frequency values, but other numbers of frequency values may be possible, such as three, five, etc. Further, while FIG. 3 shows a process for selecting values of two scan parameters, more scan parameters may be selected/optimized, such as gain, beam steering, beamforming strategy, filtering, etc. In such examples, the number of acquired images may be m+n+1, where the 1 number of images is based on the values of gain (or other parameter) available to be optimized. During the depth and frequency optimization, gain may be held constant and then once depth and frequency are optimized, the 1 number of images may be acquired with the optimal depth and optimal frequency and the different gain values. Further still, while FIG. 3 shows depth being optimized before frequency, in some examples, frequency may be optimized before depth is optimized.

The sequential process described above may result in fewer images being acquired than a joint process where m×n images are acquired and thus an image is acquired for each different possible combination of scan values, which may make the sequential process more practical and easier to implement than a joint process. Further, each parameter that is optimized according to the sequential process may be optimized with images acquired over a single cardiac cycle, which may result in images having fewer motion related artifacts and/or result in images that are more comparable to each other, which may make the parameter selection more robust. Further, after a first parameter is optimized (e.g., depth), the image with the highest image quality (e.g., from which the depth value is optimized) may be presented to the operator of the ultrasound system and/or the optimized depth value may be presented to the operator before the frequency is optimized, which may allow the operator to confirm the selection of the optimal depth value or select a different optimal depth value, which may reduce selection errors. As an example scenario, valve-like structures can be enhanced on acquisitions with high frequency by increasing the gain beyond usual/preset ranges. The enhanced valves might look similar to the valves in acquisitions with lower frequency and normal gain values. Such confounding effects due to interplay between different parameters makes it difficult to pick one optimal setting in the joint process.

FIG. 4 shows a plurality of ultrasound images 400 that may be acquired and analyzed during the process illustrated in FIG. 3. The plurality of ultrasound images 400 includes a first plurality of images 410. Each image of the first plurality of images 410 is acquired at a different depth value and at the same frequency. For example, a first image 402 is acquired at a depth of 30 cm, a second image 404 is acquired at a depth of 17 cm, and a third image 406 is acquired at a depth of 10 cm. Each of the first, second, and third images is acquired at a frequency of 1.4 MHz. Each image in the first plurality of images 410 includes a depth score determined based on output from the depth model, for example.

The plurality of ultrasound images 400 further includes a second plurality of images 420. Each image of the second plurality of images 420 is acquired at the same depth value and at a different frequency. For example, the second plurality of images 420 includes a first image 412 acquired at a frequency of 1.4 MHz, a second image 414 acquired at a frequency of 1.7 MHz, a third image 416 acquired at a frequency of 2 MHz, and a fourth image 418 acquired at a frequency of 2.3 MHz. Each image of the second plurality of images 420 shown in FIG. 4 includes two quality indicators, a predicted IQ rating and a cumulative score. The cumulative score may be determined based on output from one or more of the models illustrated in FIG. 3, such as the landmark detection model, the global image quality model, and the speckle size model. In some examples, the cumulative score may further be based on the output from the depth model. The predicted IQ rating may be obtained from the cumulative scores using empirical thresholds determined during the training process. The predicted IQ rating classifies the input ultrasound image or cine loop into three levels of image quality, such as 1 for bad/low image quality, 2 for acceptable image quality, and 3 for good/high image quality, while the cumulative score is a continuous number which is used to select the best acquisition from a set of acquisitions.

The image having the highest score (e.g., the depth score) from the first plurality of images may be selected, and the optimal depth value may be the depth value used to acquire the selected image. For example, as shown, second image 404 has a depth score of 5, which is higher than the scores of first image 402 and third image 406. Thus, the optimal depth value may be 17 cm, as second image 404 was acquired with a depth value of 17 cm. When acquiring the second plurality of images 420, the ultrasound probe may be controlled to a depth of 17 cm, and thus each image of the second plurality of images 420 is acquired at the optimal depth of 17 cm.

Likewise, the image having the highest score (e.g., the predicted IQ rating and/or the cumulative score) from the second plurality of images may be selected, and the optimal frequency value may be the frequency value used to acquire the selected image. For example, as shown, second image 414 has a predicted IQ score of 2 and a cumulative score of 4.8, which results in a higher combined score than the combined scores of first image 412, third image 416, and fourth image 418. Thus, the optimal frequency value may be 1.7 MHz, as second image 414 was acquired with a frequency value of 1.7 MHz. In some examples, only the cumulative score may be used to select the image with the optimal frequency value.

FIGS. 5A and 5B show a flow chart illustrating an example method 500 for sequential ultrasound imaging parameter selection according to an embodiment. In particular, method 500 relates to acquiring a plurality of ultrasound images at different parameter values of different scan parameters and then processing the acquired ultrasound images with multiple machine learning models to select scan parameter values, which may improve the image quality of displayed ultrasound images. Method 500 is described with regard to the systems and components of FIGS. 1-2, though it should be appreciated that the method 500 may be implemented with other systems and components without departing from the scope of the present disclosure. Method 500 may be carried out according to instructions stored in non-transitory memory of a computing device, such as image processing system 202 of FIG. 2.

At 502, ultrasound images are acquired and displayed on a display device. For example, the ultrasound images may be acquired with the ultrasound probe 106 of FIG. 1 and displayed to an operator via display device 118. The images may be acquired and displayed in real time or near real time, and may be acquired with default or user-specified scan parameters (e.g., default depth, frequency, etc.). At 504, method 500 determines if an indication that a target scan plane is being imaged has been received. The target scan plane may be a scan plane specified by a scanning protocol or designated by an operator as being a target scan plane. For example, the ultrasound images may be acquired as part of an ultrasound exam where certain anatomical features are imaged in certain views/axes in order to diagnose a patient condition, measure aspects of the anatomical features, etc. For example, during a cardiac exam, one or more target scan planes (also referred to as views) of the heart of a patient may be imaged. The target scan planes may include a four-chamber view, a two-chamber view (which may also be referred to as a short axis view), and a long axis view (which may also be referred to as a PLAX view or three-chamber view). One or more images may be acquired in each scan plane and saved as part of the exam for later analysis by a clinician such as a cardiologist. When acquiring the images for the exam, the ultrasound operator (e.g., sonographer) may move the ultrasound probe until the operator determines that the target scan plane is being imaged, and then the operator may enter an input (e.g., via user interface 115) indicating that the target scan plane is being imaged. In another example, the ultrasound system (e.g., via the image processing system 202) may automatically determine that the target scan plane is being imaged. For example, each acquired ultrasound image (or some frequency of the acquired ultrasound images, such as every fifth image) may be entered into a detection model that is configured to automatically detect the current scan plane. If the current scan plane is the target scan plane, the indication may be generated.

If an indication that the target scan plane is being imaged is not received, method 500 returns to 502 to continue to acquire and display ultrasound images (e.g., at the default or user-set scan parameters). If an indication is received that the target scan plane is being imaged, method 500 proceeds to 506 to acquire a first plurality of images (and/or cine loops), where each image (or cine loop) of the first plurality of images is acquired at a different parameter value of a first scan parameter. For example, the first scan parameter may be depth, and thus each image of the first plurality of images may be acquired at a different depth value (e.g., 10 cm, 17 cm, 30 cm, etc.). The first plurality of images may include three images, or more than three images if more than three depth values are to be selected from. During acquisition of the first plurality of images, any other scan parameters (e.g., frequency, gain, etc.) may be held constant. For example, each image of the first plurality of images may be acquired at the same value for a second parameter (e.g., at the same frequency value, such as 1.4 MHz). During acquisition of the first plurality of images, the acquired images may be displayed on the display device at the frame rate at which the images are acquired, at least in some examples.

At 508, a first parameter-specific quality metric for each image (and/or cine loop) of the first plurality of images is determined. The first parameter-specific quality metric may be a quality metric that changes as the value of the first scan parameter changes. For example, when the first scan parameter is depth, the first parameter-specific quality metric may change as depth changes. As indicated at 510, the first parameter-specific quality metric may be determined from a parameter-specific model, such as depth model 209 of FIG. 2. For example, each image of the first plurality of images may be entered as an input to the depth model, and the depth model may output, for each input image, a respective first parameter-specific quality metric (e.g., a first image quality metric as explained above with respect to FIGS. 2 and 3). In some examples, the model may be selected based on the target scan plane. For example, a first depth model may be selected when the target scan plane is a four-chamber view and a second depth model may be selected when the target scan plane is a two-chamber view.

At 512, a first image (or cine loop) of the first plurality of images is identified, where the first image is the image of the first plurality of images having the highest first quality metric, and the corresponding first parameter value for the first image is set as the first selected value for the first scan parameter. The corresponding first parameter value may be the parameter value for the first scan parameter at which the first selected image was acquired. For example, the corresponding first parameter value may be the depth value at which the first selected image was acquired, and thus the selected depth value may be the depth value at which the first selected image was acquired.

At 514, a second plurality of images (and/or cine loops) are acquired, where each image of the second plurality of images is acquired at the selected value for the first scan parameter and at a different parameter value for a second scan parameter. For example, the second scan parameter may be frequency, and thus each image of the second plurality of images may be acquired at a different frequency value (e.g., 1.4 MHz, 1.7 MHz, 2 MHz, etc.). The second plurality of images may include four images (and/or cine loops), or more or less than four images if more or less than four frequency values are to be selected from. Each image of the second plurality of images is acquired at the same parameter value (the selected parameter value) for the first scan parameter (e.g., at the selected depth value determined at 512). During acquisition of the second plurality of images, the acquired images may be displayed on the display device at the frame rate at which the images are acquired, at least in some examples.

At 516, a second parameter-specific quality metric is determined for each image (and/or cine loop) of the second plurality of images. The second parameter-specific quality metric may be a quality metric that changes as the value of the second scan parameter changes. For example, when the second scan parameter is frequency, the second parameter-specific quality metric may change as frequency changes. As indicated at 518, the second parameter-specific quality metric may be determined from one or more parameter-specific models, such as the one or more frequency models 211 of FIG. 2. For example, each image of the second plurality of images may be entered as an input to a speckle model, a landmark detection model, and/or a global image quality model, and the models may output, for each input image, a respective sub-metric (e.g., a respective second image quality metric as explained above with respect to FIGS. 2 and 3). The respective sub-metrics may be combined (e.g., added or averaged) to generate the second quality metric. In some examples, the model(s) may be selected based on the target scan plane. For example, a first landmark detection model may be selected when the target scan plane is a four-chamber view and a second landmark detection model may be selected when the target scan plane is a two-chamber view.

At 520 (shown in FIG. 5B), a second image (or cine loop) of the second plurality of images is identified, where the second image is the image of the second plurality of images having the highest second quality metric, and the corresponding second parameter value for the second optimal image is set as the selected value for the second scan parameter. The corresponding second parameter value may be the parameter value for the second scan parameter at which the second image was acquired. For example, the corresponding parameter value may be the frequency value at which the second image was acquired, and thus the selected frequency value may be the frequency value at which the second image was acquired.

At 521, method 500 optionally includes setting target post-acquisition processing parameters, which is explained in more detail below with respect to FIG. 6. Briefly, once the acquisition scan parameter values have been selected as explained above, target values for one or more post-acquisition processing parameters may be selected based on the image quality of one or more sets of adjusted images. For example, an image may be replicated, with different post-acquisition processing parameter values applied to each replicate, to create a set of adjusted images. The image from the adjusted set of images that has the highest image quality may be selected, and the parameter value(s) for that image may be applied to subsequent images. Example post-acquisition processing parameters include filtering parameters (e.g., bandwidth, center frequency), image contrast, image gain, etc.

At 522, one or more ultrasound images are acquired at the selected value for the first scan parameter and the selected value for the second scan parameter. Thus, once the scan parameter values have been selected for the target scan plane based on the determined image quality metrics as described above, the selected scan parameter values may be set and any additional images acquired by the ultrasound probe may be acquired at the set, selected scan parameter values. This may include setting the transmit depth of the ultrasound probe to the selected depth value and setting the transmit frequency of the ultrasound probe to the selected frequency. In some examples, the selected scan parameter values for the target scan plane may be saved in memory. Then, if the operator moves the ultrasound probe so that the target scan plane is not imaged, but then later moves the ultrasound probe back so that the target scan plane is imaged again, the previously determined selected scan parameter values for that scan plane may be automatically applied. Additionally, if target post-acquisition processing parameters are set (e.g., according to the method of FIG. 6), the one or more ultrasound images that are acquired at 522 may be processed according to the target post-acquisition processing parameters. For example, the received ultrasound data may be filtered according to parameter values for the filtering (e.g., bandwidth and center frequency) that are determined according to the method of FIG. 6.

At 524, method 500 determines if the current exam includes more target planes. The determination of whether the current exam includes more target planes may be made on the basis of user input. For example, the operator may enter a user input indicating that a new scan plane is being imaged, that a new scan plane is about to be imaged, or that the exam is over. In other examples, the determination of whether the exam includes more target planes may be made automatically based on the system determining a different scan plane is being imaged or that scanning has been terminated. If the exam does not include more target scan planes, for example if the current exam is complete and imaging is terminated, method 500 proceeds to 526 to display acquired images, quality metrics, and selected parameter settings, and then method 500 returns. It is to be understood that acquired images may be displayed at 522 and/or other points during method 500. Further, the selected parameter settings may be displayed at 520 to allow the operator to view and confirm the parameter settings. The quality metrics may also be displayed at other points in time, such as at 520. Further, the images acquired at 522 may be archived when requested by the operator.

If the exam does include more target scan planes, method 500 proceeds to 528 to determine if an indication that the next target plane is being imaged has been received, similar to the determination made at 504 and explained above. If the indication has not been received, method 500 proceeds to 530 to continue to acquire images at the selected values for the first and second scan parameters (e.g., as explained above with respect to 522), and then method 500 returns to 528 to continue to determine if the indication has been received. If the indication has been received, method 500 proceeds to 532 and optionally restricts the parameter values for one or both of the first and second scan parameters. For example, as explained above, the first scan parameter may have three possible parameter values and the second scan parameter may have four possible scan values. However, once the selected parameter values have been determined for a given scan plane, those selected parameter values may be applied to the next target plane, thus restricting the available values that may be optimized. For example, if the first target plane was a four-chamber view, and the next target plane is a two-chamber view, one or both of the selected values may be used to acquire images in the two-chamber view. If one of the selected values is used but not the other (e.g., the selected depth is used), the selection of the selected value for the other scan parameter (e.g., frequency) may be re-performed for the next target plane. However, when switching from the four-chamber view to the PLAX view, for example, both parameter values may be re-determined and thus 532 may not be performed.

At 534, 506-522 may be repeated for the next target plane. For example, a first plurality of images may be acquired of the next target scan plane, each at a different parameter value for the first scan parameter, a first quality metric may be determined for each image of the first plurality of images, and a first image may be identified that has the highest first quality metric. The selected value for the first scan parameter may be set as the parameter value of the first scan parameter at which the first image was acquired. Then, at the selected value for the first scan parameter, a second plurality of images of the next target scan plane may be acquired, each at a different parameter value for the second scan parameter, a second quality metric may be determined for each image of the second plurality of images, and a second image may be identified that has the highest second quality metric. The selected value for the second scan parameter may be set as the parameter value of the second scan parameter at which the second image was acquired. One or more additional images of the next target scan plane may then be acquired with the selected values for the first and second scan parameters. This process may be repeated for all additional target scan planes, until the exam is complete.

While method 500 was described above with regard to varying depth and frequency sequentially to determine target depth and frequency values that will result in a high quality image, other acquisition scan parameters may be varied according to the method described above without departing from the scope of this disclosure. For example, beamforming strategy and frequency may be varied sequentially. Beamforming strategy may include the type of beamforming which is employed, e.g., the strength/type of ACE processing. Example beamforming strategies (which may be considered the different "parameter values" for the beamforming strategy) may include delay sum, coherent plane wave compounding, and divergent beam. To select a target beamforming strategy and target frequency, a first set of images may be acquired, each at a different beamforming strategy and the same frequency (e.g., a first image at a first beamforming strategy and a first frequency, a second image at a second beamforming strategy and the first frequency, and so forth). Each image of the first set of images may be assigned a quality metric, as described above. For example, each image may be input to the speckle model, the landmark detection model, and/or the global image quality model, and the models may output, for each input image, a respective sub-metric. The respective sub-metrics may be combined (e.g., added or averaged) to generate the quality metric for each image. The image having the highest quality metric may be selected, and the beamforming strategy used to acquire the selected image may be set as the target beamforming strategy for subsequent image acquisition. Then, a second set of images may be acquired, each at the target beamforming strategy and a different frequency (e.g., a first image at the target beamforming strategy and a first frequency, a second image at the target beamforming strategy and a second frequency, and so forth). Each image of the second set of images may be assigned a quality metric, as described above, and the image from the second set of images having the highest quality metric may be selected. The frequency used to acquire that image may be selected as the target frequency and used with the target beamforming strategy to acquire subsequent images. In examples where depth is not a scan parameter to be varied and selected, the depth model explained above may be omitted from the quality metric determination.

Turning now to FIG. 6, a method 600 for determining post-acquisition processing parameters for ultrasound images is presented. Method 600 may be carried out as part of method 500, for example once acquisition parameter values for a target plane have been determined. In other examples, method 600 may be carried out independently of method 500, for example in response to a user request to set post-acquisition processing parameter values. Method 600 may be carried out according to instructions stored in non-transitory memory of a computing device, such as image processing system 202 of FIG. 2.

At 602, ultrasound information for a single image is obtained. The ultrasound information may be acquired with an ultrasound probe in response to execution of method 600, or the ultrasound information may be retrieved from memory. In one non-limiting example, the ultrasound information may be ultrasound information sufficient to generate one image, and the ultrasound information may be obtained with target acquisition scan parameters as discussed above (e.g., at a target depth, a target frequency, etc.).

At 604, different parameter values for a first post-acquisition parameter are applied to the obtained ultrasound information to generate a first set of adjusted images. For example, the first post-acquisition parameter may be a filtering center frequency, and the different parameter values may be different center frequencies (e.g., 3.2 MHz, 3.4 MHz, and 3.6 MHz, or different multiples of the transmission frequency, such as the transmission frequency, twice the transmission frequency, and three times the transmission frequency). In another example, the first post-acquisition parameter may be a filtering bandwidth and the different parameter values may be different bandwidths (e.g., 1 MHz, 1.2 MHz, and 1.4 MHz). Each different parameter value may be applied to the ultrasound information to generate an image for each parameter value. For example, when the first post-acquisition parameter is the filtering center frequency, the first set of adjusted images may include a first image generated with a center frequency of 3.2 MHz, a second image generated with a center frequency of 3.4 MHz, and a third image generated with a center frequency of 3.6 MHz. The same ultrasound information may be used to generate each image in the first set of adjusted images. Any other post-acquisition parameters may be held constant at a default or commanded value.

At 606, a quality metric of each image in the first set of adjusted images is determined. The quality metric of each image may be determined by entering each image as input to one or more image quality models, as explained above with respect to FIGS. 2, 3, 5A, and 5B. For example, each image may be entered as input to a global image quality model, a landmark detection model, and a speckle model, and each model may output a respective quality sub-metric that may be summed or averaged to arrive at an overall image quality metric for each image.

At 608, the image of the first set of adjusted images having the highest image quality metric is selected. If two or more images have the same, highest image quality metric, an additional metric may be used to select from among the two or more images, such as the global image quality model sub-metric. At 610, the first post-acquisition parameter is set to the parameter value of the selected image. For example, if the selected image was generated with a filter center frequency of 3.2 MHz, the filter center frequency may be set at 3.2 MHz.

At 612, the above process may be repeated for any additional post-acquisition parameters. For example, after selecting the first post-acquisition parameter value, the ultrasound information may again be used to generate replicate images, with each replicate image having a different parameter value for a second post-acquisition parameter, such as filter bandwidth, to form a second set of adjusted images. When the first post-acquisition parameter has been set, the images of the second set of adjusted images may be generated with the set parameter value for the first post-acquisition parameter. The image quality metric may be determined for each image in the second set of adjusted images, and the image having the highest image quality metric may be selected. The parameter value for the second post-acquisition parameter of the image having the highest image quality metric may be set as the parameter value for the second post-acquisition parameter. At 614, the set parameter value for each post-acquisition parameter is applied to any subsequent images, e.g., of the current view plane. Method 600 then ends.

While method 600 was described above as including a sequential process for selecting parameter values for two or more post-acquisition parameters, a joint process may be used instead. In the joint process, one set of replicate images may be generated, where each image has a different combination of parameter values for the two or more post-acquisition parameters. The image quality of each image may be determined as described above, and the image having the highest image quality metric may be selected. The parameter values for the two or more post-acquisition parameters used to generate the selected image may be selected and set as the parameter values for subsequent image processing.

The image acquisition process used to acquire the ultrasound images described herein may be carried out according to a suitable scan sequence. FIG. 7 shows a graph 900 illustrating a first example scan sequence that may be executed to acquire ultrasound information that may be used to generate a single image. Graph 700 shows a sector scan, though other scan geometries are also possible. Each line in graph 700 represents a transmit direction, and the transmits are fired sequentially from, for example, left to right. When a transmit parameter is varied, such as frequency, the transmits may all be fired at the same parameter value (e.g., at the same frequency, P1) to generate a first image. Then, the frequency may be adjusted to a second frequency, and the transmits may all be fired sequentially at the second frequency to generate a second image.

The scan sequence of FIG. 7 would result in subsequent images being obtained with different parameter values, when exploring for the target parameter value. However, subsequent shots within an image are be possible to be acquired with different parameters. This scan process for acquisition would include firing in the same transmit direction N times to record data for that direction with N different parameter values before moving on to the next transmit direction. This scan process is shown in FIG. 8, which shows a graph 800 illustrating a second example scan sequence that may be executed to acquire ultrasound information that may be used to generate multiple images. Graph 800 shows a sector scan, though other scan geometries are also possible. Each solid line in graph 800 represents a transmit direction and a first parameter value, while each dashed line represents a different parameter value (fired at the transmit direction of the solid line to its left) and the transmits are fired sequentially from, for example, left to right. Instead of including only one transmit parameter value, graph 1000 includes four transmit parameter values, P1-P4. For example, the transmit parameter may be frequency and each parameter value may be a different frequency.

During image acquisition, the transmits may be fired sequentially, but for each transmit direction, a transmit may be fired for each parameter value before moving on to the next transmit direction. For example, for a first transmit direction, a transmit may be fired at P1, a transmit may be fired at P2, a transmit may be fired at P3, and a transmit may be fired at P4 (while the different solid/dashed lines are placed besides each other for illustration purposes, it is to be understood that each transmit for P1-P4 for the first transmit direction would be fired at the same transmit direction). The transmit direction may be updated to a second transmit direction, and a set of transmits may be fired at the second transmit direction, one for each parameter value. The process may repeat until all transmit directions have been fired at all parameter values. A first image may be generated from information acquired while firing at the first parameter value, a second image may be generated from information acquired while firing at the second parameter value, a third image may be generated from information acquired while firing at the third parameter value, and a fourth image may be generated from information acquired while firing at the fourth parameter value. This scan sequence for parameter exploration would fire several times in each direction before moving on to the next transmit direction. This may result in longer time to acquire all directions of an image, but would result in very low lag between the different parameters that are to be compared for image quality.

The scan sequence shown in FIG. 8 may be executed during the image acquisition for parameter selection as described above with respect to FIGS. 5A and 5B, at least in some examples. In other examples, the scan sequence shown in FIG. 7 may be executed during the image acquisition for parameter selection.

Further, because motion of the imaged anatomical features may contribute to fluctuations in image quality, it may be desirable to obtain the images described herein (e.g., used to determine the optimal scan parameters) during periods where motion is not occurring, or during periods where motion among the images is comparable. When imaging the heart, obtaining images with no motion or comparable motion may be challenging, given the movement of the heart over the course of a cardiac cycle. For example, for a patient having a heart rate of 60 beats per minute, a cardiac cycle may last one second, which is approximately the same amount of time used to acquire all the images described herein. Thus, the decision of whether frequency is held constant for a duration while depth is varied to select the optimal depth first, or whether depth is held constant while frequency is varied to select the optimal frequency first may depend on what anatomy is being imaged (e.g., whether the heart is being imaged, and if so, which view of the heart). For example, when images of different frequency but the same depth are compared to one another to determine which image has the highest image quality, a more reliable determination may be made when all the images being compared are acquired in the same relative phase of the cardiac cycle. Thus, at least in some examples, the timing of when the different images are acquired may be set so that images acquired at different frequencies are acquired in the same general phase of the cardiac cycle or otherwise are subject to similar motion.

A technical effect of sequentially selecting scan parameter values includes increased image quality and reduced operator workflow demands Another technical effect is more consistent image quality across multiple exams.

In another representation, a system includes an ultrasound probe, a memory storing instructions, and a processor communicably coupled to the memory and when executing the instructions, configured to: process ultrasound information obtained with the ultrasound probe into a first set of replicate images, each replicate image processed according to a different post-acquisition processing parameter value of a plurality of post-acquisition processing parameter values for a first post-acquisition processing parameter; determine an image quality metric of each replicate image of the first set of replicate images; select the replicate image having the highest image quality metric; and process additionally acquired ultrasound information according to the post-acquisition processing parameter value used to process the ultrasound information into the selected replicate image. In an example, each replicate image of the first set of replicate images is processed from the same ultrasound information, such that the replicate images are identical other than the different post-acquisition processing parameter values used to create the replicate images. In an example, the processor is configured to, after selecting the replicate image having the highest image quality metric: process the ultrasound information into a second set of replicate images, each replicate image of the second set of replicate images processed according to a different post-acquisition processing parameter value of a plurality of post-acquisition processing parameter values for a second post-acquisition processing parameter; determine an image quality metric of each replicate image of the second set of replicate images; select the replicate image of the second set of replicate images having the highest image quality metric; and process additionally acquired ultrasound information according to the post-acquisition processing parameter value for the second post-acquisition processing parameter used to process the ultrasound information into the selected replicate image. In an example, each replicate image of the first set of replicate images is processed according to a different parameter value for a second post-acquisition processing parameter, and the additionally acquired ultrasound information is processed according to the parameter value for the second post-acquisition processing parameter used to process the ultrasound information into the selected replicate image. In an example, the ultrasound information may be acquired with the ultrasound probe at a first target scan parameter value and a second target scan parameter value selected according to the sequential process described above with respect to FIGS. 5A and 5B.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
acquiring ultrasound information of an anatomical region with an ultrasound probe, processing the ultrasound information to generate a first set of replicate images, each replicate image of the first set of replicate images processed according to a different parameter value for a first post-acquisition processing parameter in order to generate a first plurality of images;
selecting a first parameter value for the first post-acquisition processing parameter based on an image quality of each ultrasound image of the first plurality of ultrasound images;
processing the ultrasound information to generate a second set of replicate images, each replicate image of the second set of replicate images processed according to a different parameter value for a second post-acquisition processing parameter in order to generate a second plurality of images;
selecting a second parameter value for the second post-acquisition processing parameter based on an image quality of each ultrasound image of the second plurality of ultrasound images; and
applying the first parameter value for the first post-acquisition processing parameter and the second parameter value for the second post-acquisition processing parameter to one or more additional ultrasound images.

2. The method of claim 1, further comprising:
selecting a third parameter value for a third scan parameter based on an image quality of each ultrasound image of a third plurality of ultrasound images of the anatomical region, each ultrasound image of the third plurality of ultrasound images having a different parameter value for the third scan parameter;
selecting a fourth parameter value for a fourth scan parameter based on an image quality of each ultrasound image of a fourth plurality of ultrasound images of the anatomical region, each ultrasound image of the fourth plurality of ultrasound images having a different parameter value for the fourth scan parameter; and
applying the third parameter value for the third scan parameter and the fourth parameter value for the fourth scan parameter to the one or more additional ultrasound images, wherein each ultrasound image of the third plurality of ultrasound images has the same parameter value for the fourth scan parameter, and wherein each ultrasound image of the fourth plurality of ultrasound images has the third parameter value for the third scan parameter.

3. The method of claim 2, wherein the third scan parameter comprises depth and the fourth scan parameter comprises frequency, and further comprising acquiring each image of the third plurality of images at a different depth value and the same frequency value and acquiring each image of the fourth plurality of images a different frequency value and the same depth value.

4. The method of claim 2, wherein the third scan parameter comprises beamforming strategy and the fourth scan parameter comprises frequency, and further comprising acquiring each image of the third plurality of images at a different beamforming strategy and the same frequency value and acquiring each image of the fourth plurality of images a different frequency value and the same beamforming strategy.

5. The method of claim 1, wherein selecting the first parameter value comprises determining a respective first image quality value for each ultrasound image of the first plurality of ultrasound images using a first model, and selecting a first ultrasound image of the first plurality of ultrasound images that has a highest first image quality value, the selected first ultrasound image having the first parameter value for the first post-acquisition processing parameter; and
wherein selecting the second parameter value comprises determining a respective second image quality value for each ultrasound image of the second plurality of ultrasound images using one or more second models, and selecting a second ultrasound image of the second plurality of ultrasound images that has a highest second image quality value, the selected second ultrasound image having the second parameter value for the second post-acquisition processing parameter.

6. A system, comprising:
a memory storing instructions; and
a processor communicably coupled to the memory and when executing the instructions, configured to:
first select a first parameter value for a first scan parameter based on an image quality of each ultrasound image of a first plurality of ultrasound images of an anatomical region, each ultrasound image of the first plurality of ultrasound images having a different parameter value for the first scan parameter and a same parameter value for a second scan parameter;
then, after selecting the first parameter value, select a second parameter value for the second scan parameter based on an image quality of each ultrasound image of a second plurality of ultrasound images of the anatomical region, each ultrasound image of the second plurality of ultrasound images having the first parameter value for the first scan parameter and a different parameter value for the second scan parameter; and
apply the first parameter value for the first scan parameter and the second parameter value for the second scan parameter to one or more additional ultrasound images.

7. The system of claim 6, wherein the memory stores one or more neural networks, and wherein when executing the instructions, the processor is configured to input each ultrasound image of the first plurality of ultrasound images to one or more of the neural networks to determine the respective image quality of each ultrasound image of the first plurality of ultrasound images, and input each ultrasound image of the second plurality of ultrasound images to one or more of the neural networks to determine the respective image quality of each ultrasound image of the second plurality of ultrasound images.

8. The system of claim 6, wherein the memory stores a global image quality neural network, a landmark detection neural network, and a speckle neural network, and wherein when executing the instructions, the processor is configured to:

input each ultrasound image of the second plurality of ultrasound images to the global image quality neural network to determine a first sub-metric for each image of the second plurality of ultrasound images;

input each ultrasound image of the second plurality of ultrasound images to the landmark detection neural network to determine a second sub-metric for each image of the second plurality of ultrasound images;

input each ultrasound image of the second plurality of ultrasound images to the speckle neural network to determine a third sub-metric for each image of the second plurality of ultrasound images; and determine the respective image quality for each image of the second plurality of ultrasound images by summing the respective first sub-metric, the respective second sub-metric, and the respective third sub-metric.

9. The system of claim 6, wherein the first scan parameter comprises an acquisition depth and the second scan parameter comprises an acquisition frequency, and wherein each image of the second plurality of images is acquired, via an ultrasound probe, at the selected parameter value of the acquisition depth.

10. The system of claim 6, further comprising an ultrasound probe, wherein the first scan parameter is a first post-acquisition processing parameter, the second scan parameter is a second post-acquisition processing parameter, and wherein the processor, when executing the instructions, is further configured to:

acquire ultrasound information with the ultrasound probe;

process the ultrasound information into the first plurality of ultrasound images by processing the ultrasound information multiple times, each with a different parameter value for the first post-acquisition processing parameter;

process the ultrasound information into the second plurality of ultrasound images by processing the ultrasound information multiple times, each with a different parameter value for the second post-acquisition processing parameter.

11. The system of claim 6, wherein the plurality of second images are acquired, via an ultrasound probe, before acquisition of the plurality of first images, and wherein each first image of the plurality of first images has the same, default parameter value for the second scan parameter.

* * * * *